United States Patent [19]
Yamakawa et al.

[11] Patent Number: 5,980,947
[45] Date of Patent: Nov. 9, 1999

[54] PROCESS FOR PRODUCING DRUG-CONTAINING MICROSPHERES BY OIL-IN-WATER EVAPORATION PROCESS

[75] Inventors: Ichiro Yamakawa, Ibaraki Prefecture; Ryoichi Machida, Chiba Prefecture; Sumio Watanabe, Aichi Prefecture, all of Japan

[73] Assignee: Eisai Co., Ltd., Japan

[21] Appl. No.: 08/352,188

[22] Filed: Dec. 1, 1994

Related U.S. Application Data

[63] Continuation of application No. 08/051,272, Apr. 23, 1993, abandoned, which is a continuation of application No. 07/713,837, Jun. 12, 1991, abandoned.

[30] Foreign Application Priority Data

| Jun. 13, 1990 | [JP] | Japan | 2-152849 |
| Jun. 13, 1990 | [JP] | Japan | 2-152850 |
| Feb. 22, 1991 | [JP] | Japan | 3-048579 |

[51] Int. Cl.$^6$ .............. A61K 9/50; A61K 9/14
[52] U.S. Cl. ............ 424/489; 424/490; 424/450
[58] Field of Search .............. 424/450, 489, 424/490

[56] References Cited

U.S. PATENT DOCUMENTS

| 4,542,025 | 9/1985 | Tice | 514/180 |
| 4,671,954 | 6/1987 | Goldberg | 514/963 |
| 4,933,105 | 6/1990 | Fong | 514/951 |
| 4,954,298 | 9/1990 | Yamamoto | 424/462 |
| 4,954,338 | 9/1990 | Mattox | 424/78.03 |
| 4,994,281 | 2/1991 | Muranishi | 424/497 |

*Primary Examiner*—Raj Bawa
*Attorney, Agent, or Firm*—Wenderoth, Lind & Ponack, L.L.P.

[57] ABSTRACT

Formation of a drug into microspheres by an oil-on-water solvent evaporation process in which a mixed solvent of at least one water-insoluble solvent and at least one water-miscible solvent is used as a solvent of an oil phase. A fatty acid or a salt thereof or at least one glycerin fatty acid ester and/or at least one propylene glycol fatty acid ester are added to the mixed solvent. The oil phase may also comprise the mixed solvent; a fatty acid or a salt thereof; and at least one glycerin fatty acid ester and/or at least one propylene glycol fatty acid ester. This oil phase is mixed and emulsified with an aqueous phase to form an oil-in-water emulsion. The emulsion with a drug contained therein is then subjected to an oil-in water solvent evaporation to produce the microspheres. The resulting drug-containing microspheres contain the drug at a high concentration and slowly release from the initial stage after administration.

14 Claims, No Drawings

PROCESS FOR PRODUCING DRUG-CONTAINING MICROSPHERES BY OIL-IN-WATER EVAPORATION PROCESS

This application is a continuation application of Ser. No. 08/051,272 filed Apr. 23, 1993, now abandoned, which in turn is a continuation application of Ser. No. 07/713,837, filed Jun. 12, 1991, now abandoned.

BACKGROUND OF THE INVENTION

1) Field of the Invention

This invention relates to a process for the production of sustained release microspheres of a drug, and especially to a process for producing, by O/W solvent evaporation, microspheres which contain a drug at high concentration.

2) Description of the Related Art

O/O, W/O/W and O/W solvent evaporation methods have heretofore been known for the formation of microspheres.

Appropriate for efficient incorporation of a drug in microspheres is O/O solvent evaporation which uses a water-miscible solvent as an inner phase and a silicone oil, vegetable oil or the like as an outer phase. This technique however involves many problems such as the use of a solvent in a large volume and the need for heating upon drying.

Japanese Patent Application Laid-Open (Kokai) No. SHO 62-201816 discloses a W/O/W solvent evaporation method, in which the viscosity of a W/O emulsion is adjusted to 150–10,000 cp for efficient incorporation of a drug. However, W/O/W type microspheres have a three-phase structure so that the process requires complex steps. It is also necessary to adjust the viscosity of the inner water phase by using gelatin or the like.

O/W solvent evaporation requires a relatively small amount of an organic solvent. When this method is applied to a water-soluble drug, most of the drug is distributed to the outer water phase. This has led to the drawback that the amount of the drug incorporated in the resulting microspheres is extremely small.

According to general O/W solvent evaporation methods, the resulting microspheres show such release behavior that the release of the drug is relatively slow in the initial stage after administration but becomes faster as time goes on.

SUMMARY OF THE INVENTION

An object of the present invention is to provide a novel process which can improve the percentage of incorporation of a drug in microspheres when said microspheres are being produced by solvent evaporation.

The present inventors decided to make improvements in the O/W solvent evaporation method out of the solvent evaporation methods described above. Described specifically, the present inventors have proceeded with an extensive investigation to overcome the above-described drawbacks of the O/W solvent evaporation method. As a result, it has been found that such drawbacks can be solved by the adoption of a process to be described below, leading to the completion of the present invention.

The present inventors have also succeeded in solving, by the adoption of the below-described process, the problem that the microspheres produced by O/W solvent evaporation are slow to release the drug in the initial stage after administration. This has also led to the completion of the present invention.

In a first aspect of the present invention, there is thus provided a process for the production of drug-containing microspheres. Upon formation of a drug into microspheres by O/W solvent evaporation, a mixed solvent comprising at least one water-insoluble solvent and at least one water-miscible solvent is used as a solvent of an oil phase. Described more specifically, the process comprises either dissolving or dispersing a drug together with a high molecular substance in an organic solvent composition, which is composed of at least one water-insoluble solvent and at least one water-miscible solvent, to form an oil phase (inner phase) and then stirring the oil phase in an aqueous solution as a water phase (outer phase), said aqueous solution containing an activator such as polyvinyl alcohol, whereby the oil phase is enclosed as small droplets within the aqueous solution as shells.

When a drug is formed into microspheres by O/W solvent evaporation in accordance with the process of the first aspect of the present invention, distribution of the drug into the outer water phase can be prevented. This makes it possible to increase the percentage of incorporation of the drug in the microspheres, resulting in an increased amount of the drug in the microspheres.

In a second aspect of the present invention, there is also provided a process for the production of drug-containing microspheres. Upon formation of a drug into microspheres by O/W solvent evaporation, an oil phase contains a fatty acid or a salt thereof. Described more specifically, the process comprises either dissolving or dispersing a drug together with a high molecular substance in a solvent to form an oil phase (inner phase) and then stirring the oil phase in an aqueous solution as a water phase (outer phase), said aqueous solution containing an activator such as polyvinyl alcohol, whereby the oil phase are enclosed as small droplets within the aqueous solution as shells.

When a drug is formed into microspheres by O/W solvent evaporation in accordance with the process of the second aspect of the present invention, distribution of the drug into the outer water phase can be prevented. This makes it possible to increase the percent incorporation of the drug in the microspheres, resulting in an increased amount of the drug in the microspheres.

In a third aspect of the present invention, there is also provided a process for the production of drug-containing microspheres. Upon formation of a drug into microspheres by O/W solvent evaporation, an oil phase contains at least one glycerin fatty acid ester and/or at least one propylene glycol fatty acid ester.

When a drug is formed into microspheres by O/W solvent evaporation in accordance with the process of the third aspect of the present invention, the release rate of the drug can be easily controlled by adjusting the amount of the glycerin fatty acid ester and/or that of the propylene glycol fatty acid ester. Further, the release rate of the drug from the resulting microspheres remain substantially constant from the initial stage after the administration.

DETAILED DESCRIPTION OF THE INVENTION AND PREFERRED EMBODIMENTS

To practice the process according to the first aspect of the present invention, O/W solvent evaporation can be carried out by any desired method known in the present field of art. Namely, a high molecular substance having in vivo degradability or bio-compatibility, such as polylactic acid, is added to a drug. The resulting mixture is either dissolved or dispersed in a mixed solvent composed of at least one water-insoluble solvent and at least one water-miscible solvent, in other words, in a water-insoluble solvent, e.g., methylene chloride in which at least one water-miscible solvent such as ethanol has been mixed, followed by the emulsification and dispersion in a water-soluble solvent such as polyvinyl alcohol.

The emulsification and dispersion can be performed in an apparatus commonly employed in the art, such as "POLYTRON" (trade mark) or an ultrasonic emulsifier. Next, O/W solvent evaporation is conducted under stirring so that the oil phase is solidified. The resulting microspheres are collected by a centrifugal separator, washed with purified water and re-dispersed in water, and then lyophilized into powder.

As the water-miscible solvent, any desired solvent can be used as long as it is miscible with water. Preferred, exemplary water-miscible solvents include methanol, ethanol, propanol, dimethyl sulfoxide and acetonitrile. The preferred proportion of the water-miscible solvent in the oil phase may range from 5% to 95%, with 10–50% being more preferred. This proportion may vary as desired, depending on the properties of both the water-insoluble solvent and the water-miscible solvent and also on the properties of the drug.

On the other hand, as the water-insoluble solvent employed in combination with the water-miscible solvent, any desired water-insoluble solvent can be used as long as it is hardly miscible with water and it can dissolve the high-molecular substance. Preferred examples of the water-insoluble solvent include halogenated alkanes such as methylene chloride, chloroform, carbon tetrachloride and dichloroethane; ethyl acetate; and cyclohexane. Methylene chloride is most preferred when polylactic acid or a lactic acid-glycolic acid copolymer is used. The high-molecular substance, which is contained in the organic phase employed in this invention, may preferably be either insoluble or only sparingly soluble in water and bio-compatible. Examples of such high-molecular substances include, as in vivo degradable ones by way of example, poly(fatty acid esters) such as polylactic acids and polyglycolic acids, poly-α-cyanoacrylic acid esters, poly-β-hydroxybutyric acids, and polyorthoesters; as well as high-molecular substances derived from living organisms such as thermally-denatured or formaldehyde-crosslinked collagen, gelatin and albumin, and enzyme-modified fibrin.

Other high-molecular substances having biocompatibility include polystyrene, polyacrylic acid, polymethacrylic acid, ethylcellulose, polyacrylamide, maleic anhydride copolymers, polyurethanes.

These high-molecular substances can be used either singly or in combination. When two or more of such high-molecular substances are used in combination, they can be employed either as a copolymer or as a mere physical mixture. The high-molecular substances can be used in the form of pharmacologically-acceptable salts. Among these high-molecular substances, preferred injectable high-molecular substances include in vivo degradable polylactic acid and lactic acid-glycolic acid copolymers, whose average molecular weights may preferably range from 1,000 to 100,000.

Production of microspheres by the process of the second aspect of the present invention can be carried out by any desired O/W solvent evaporation method known commonly in the present field of art. Namely, a fatty acid or a salt thereof and a high molecular substance having in vivo degradability or bio-compatibility, such as polylactic acid or polystyrene, are added to a drug. The resulting mixture is either dissolved or dispersed in an organic solvent such as methylene chloride, followed by the emulsification and dispersion in an aqueous solution of polyvinyl alcohol or the like. The emulsification and dispersion can be performed in an apparatus commonly employed in the art, such as "POLYTRON" (trade mark) or an ultrasonic emulsifier. Under stirring, O/W solvent evaporation is conducted so that the oil phase is solidified. The resulting microspheres are collected by a centrifugal separator, washed with purified water and then re-dispersed in water, and then lyophilized into powder.

The term "fatty acid or a salt thereof", which is used in the process according to the third aspect of the present invention, generally means a monocarboxylic acid having a chain structure which contains a linear or branched alkyl group. Carbon numbers of 4 and greater are preferred. Specific examples include sodium butyrate, sodium valerate, sodium caproate, sodium enanthoate, sodium caprylate, sodium pelargonate, sodium caprate, sodium undecylate, sodium laurate, sodium tridecylate, sodium myristate, sodium pentadecylate, sodium palmitate, sodium heptadecylate, sodium stearate, sodium nonadecanoate, sodium arachiate, sodium isocrotonate, sodium undecylenate, sodium oleate, sodium elaidiate, sodium sorbiate, sodium linoleate, sodium linolenate, sodium arachidonate and potassium oleate.

More preferred examples of fatty acid salts include those containing an even number of carbon atoms, said even number being at least 8 but not greater than 18, for example, sodium caprate, sodium caprylate, sodium laurate, sodium myristate, sodium palmitate, sodium stearate, sodium oleate and potassium oleate. Any salt can be used as long as it is a metal salt which is pharmacologically acceptable and is dissociable in an aqueous solution. Preferred examples of salts include the sodium and potassium salts.

The term "glycerin fatty acid ester", which is employed in the process according to the third aspect of the present invention, generally means a glycerin fatty acid ester in which one or two of the hydroxyl groups of glycerin has or have been esterified by a corresponding number of saturated or unsaturated $C_6$–$C_{18}$ carbon chain(s). Specific examples include glycerin monocaprylate, glycerin monocaprate, glycerin monolaurate, glycerin monomyristate, glycerin monopalmitate, glycerin monostearate, glycerin monooleate and glycerin dicaprate. They can be used either singly or in combination. On the other hand, examples of the propylene glycol fatty acid ester employed in the process according to the third aspect of the present invention include propylene glycol monocaprylate, propylene glycol dicaprylate, propylene glycol monocaprate, propylene glycol monolaurate, propylene glycol monomyristate, propylene glycol monopalmitate, propylene glycol monostearate and propylene glycol monooleate.

In the process according to the third aspect of the present invention, it is possible to use, in combination, one or more glycerin fatty acid esters and one or more propylene glycol fatty acid esters. Namely, an appropriate combination of the above-described substances makes it possible to produce microspheres having a desired release rate. Upon practice of the process according to the third aspect of the present invention, in order to increase the percent incorporation of a drug into microspheres, a water-miscible solvent can be added to the solvent of the oil phase or a fatty acid or a salt thereof can be added to the oil phase.

The process according to the third aspect of the present invention can be carried out by a conventional O/W solvent evaporation method. For example, a high molecular substance having in vivo degradability or bio-compatibility, such as polylactic acid, is added to a mixture of a drug and a glycerin fatty acid ester. The resulting mixture is either dissolved or dispersed in a water-insoluble solvent such as methylene chloride, followed by the emulsification and dispersion in an aqueous solution of polyvinyl alcohol or the like. The emulsification and dispersion can be performed in an apparatus commonly employed in the art, such as "POLYTRON" (trade mark). Under stirring, O/W solvent evaporation is then conducted so that the oil phase is solidified. Microspheres so formed are collected by a centrifugal separator, washed with purified water and then re-dispersed in water, and then lyophilized into powder.

In the case of a water-soluble drug, a water-miscible solvent such as ethanol can be added to an oil phase such as methylene chloride in order to further increase its percent incorporation into microspheres.

Drug-containing microspheres according to the present invention can also be produced by adding to a drug a high molecular substance having in vivo degradability or biocompatibility, adding (a) a mixed solvent comprising at least one water-insoluble solvent and at least one water-miscible solvent, (b) a fatty acid or a salt thereof, and (c) at least one glycerin fatty acid ester and/or at least one propylene glycol fatty acid ester to the resulting mixture to form an oil phase, emulsifying and dispersing the oil phase in an aqueous solution with polyvinyl alcohol or the like dissolved therein, and subjecting the resulting dispersion to O/W solvent evaporation.

The high-molecular substance dissolved in the oil phase to be employed in the process of the third aspect of the present invention may desirably be either insoluble or only sparingly or poorly soluble in water and have biocompatibility. Exemplary high-molecular substances include in vivo degradable high-molecular substances such as polylactic acid and polyglycolic acid as well as biocompatible high-molecular substances such as polystyrene and polyacrylic acid. These high-molecular substances can be used either singly or in combination. When two or more of such high-molecular substances are used in combination, they can be employed either as a copolymer or as a mere physical mixture. Among these high-molecular substances, in vivo degradable polylactic acid and lactic acid-glycolic acid copolymers are particularly preferred with an average molecular weight of 1,000–100,000 being desired.

Drugs usable in the present invention can include, but are not limited to, water-soluble drugs, for example, antitumor agents, antipyretic agents, antibiotics, antitussive and expectorant agents, analgesics, muscle relaxants, hypotensives, anticoagulants, and physiologically active peptides.

Specific examples of such physiologically active peptides include lysozyme chloride, enkephalin, dinorphine, luteinizing hormone-releasing hormone (LH-RH), insulin, somatostatin, calcitonin, secretin, neurotensin, and thyroid hormone-releasing hormone (TRH) as well as their salts and derivatives. Exemplary antitumor agents include adriamycin, neocarzinostatin, fluorouracil, tetrahydrofuryl-5-fluorouracil, vincristine sulfate, vinblastine sulfate, bleomycin hydrochloride, PICIBANIL (trade mark) and mitomycin. Examples of such antipyretic, analgesic and antiinflammatory agents include sodium salicylate, SULPYRINE (trade mark), diclofenac sodium, morphine hydrochloride and pethidine hydrochloride. Illustrative of such antibiotics include tetracycline hydrochloride, oxytetracycline hydrochloride, gentamycin, amikacin, ampicillin, cephalotin, cefmetazole, cefazolin, cefoperazone and azthreonam. Exemplary antitussive and expectorant agents include methylephedrine hydrochloride, ephedrine hydrochloride, codeine phosphate, dihydrocodeine phosphate, isoproterenol hydrochloride and salbutamol sulfate. Exemplary sedatives include chloropromazine hydrochloride, scopolamine bromide and atropine sulfate. Examples of such muscle relaxants include eperisone hydrochloride, tubocurarine hydrochloride and pancuronium bromide. Illustrative of such hypotensives include bunazosin hydrochloride and chromazine hydrochloride. Examples of such anticoagulants include heparin sodium and sodium citrate.

The present invention will hereinafter be described more specifically by the following examples. It is however to be noted that the present invention is not limited to the following examples.

EXAMPLE 1

Twenty milligrams of neurotensin analog and 200 mg of poly-dl-lactic acid (number average molecular weight: 2,000) were dissolved in 0.6 ml of a mixed solvent of methylene chloride and ethanol (mixing ratio: 5:1 by volume). After the resulting solution was emulsified and dispersed in 200 ml of a 0.5% aqueous solution of polyvinyl alcohol by a small homogenizer, the resulting dispersion was stirred for about 3 hours to conduct O/W solvent evaporation so that an oil phase was solidified. Microspheres thus formed were collected by a centrifugal separator, washed with purified water, re-dispersed in water and then lyophilized into powder.

EXAMPLE 2

Ten milligrams of thyrotropin releasing hormone and 100 mg of poly-l-lactic acid (number average molecular weight: 2,000) were dissolved in 0.3 ml of a mixed solvent of methylene chloride and ethanol (mixing ratio: 5:1 by volume). Following the procedures of Example 1, the resulting solution was subjected to O/W solvent evaporation in 100 ml of a 0.5% aqueous solution of polyvinyl alcohol and lyophilization was then conducted to obtain powder.

EXAMPLE 3

Ten milligrams of neurotensin analog and 100 mg of poly-dl-lactic acid (number average molecular weight: 2,000) were dissolved in 0.3 ml of a mixed solvent of methylene chloride and ethanol (mixing ratio: 5:2 by volume). Following the procedures of Example 1, the resulting solution was subjected to O/W solvent evaporation in 100 ml of a 0.5% aqueous solution of polyvinyl alcohol and lyophilization was then conducted to obtain powder.

EXAMPLE 4

Ten milligrams of neurotensin analog and 100 mg of poly-dl-lactic acid (number average molecular weight: 2,000) were dissolved in 0.3 ml of a mixed solvent of methylene chloride and ethanol (mixing ratio: 5:3 by volume). Following the procedures of Example 1, the resulting solution was subjected to O/W solvent evaporation in 100 ml of a 0.5% aqueous solution of polyvinyl alcohol and lyophilization was then conducted to obtain powder.

EXAMPLE 5

Ten milligrams of neurotensin analog and 100 mg of poly-dl-lactic acid (number average molecular weight: 2,000) were dissolved in 0.3 ml of a mixed solvent of methylene chloride and ethanol (mixing ratio: 1:1 by volume). Following the procedures of Example 1, the resulting solution was subjected to O/W solvent evaporation in 100 ml of a 0.5% aqueous solution of polyvinyl alcohol and lyophilization was then conducted to obtain powder.

COMPARATIVE EXAMPLE 1

Microspheres were produced in a similar manner to Example 1 except that 0.6 ml of methylene chloride was used instead of the mixed solvent of methylene chloride and ethanol.

COMPARATIVE EXAMPLE 2

Microspheres were produced in a similar manner to Example 2 except that methylene chloride was used in place of the mixed solvent of methylene chloride and ethanol.

A description will next be made of an experiment to demonstrate advantageous effects of the first aspect of the invention in detail.

Experiment (1) Procedure:

The drug content in the microspheres obtained in each of Examples 1–5 and Comparative Examples 1–2 was measured by high-performance liquid chromatography. Their incorporation percentages were compared with one another.

(2) Results:

The results are summarized in Table 1, in which each incorporation percentage was determined in accordance with the following formula:

$$\text{Incorporation percentage} = \frac{\text{Measured content}}{\text{calculated content}} \times 100$$

TABLE 1

|  | Sample |  | Incorporation percentage |
|---|---|---|---|
| Invention | Example | 1 | 21.5 |
|  |  | 2 | 25.5 |
|  |  | 3 | 40.7 |
|  |  | 4 | 54.8 |
|  |  | 5 | 21.1 |
| Control | Comp. Ex. | 1 | 10.4 |
|  |  | 2 | 10.6 |

As is apparent from Table 1, the various microsphere samples obtained by the process according to the first aspect of the present invention showed a higher incorporation percentage than the microsphere samples (controls) produced by using the oil phases free of any water-miscible solvent.

EXAMPLE 6

Twenty milligrams of neurotensin analog, 9.2 mg of sodium caprylate and 200 mg of poly-dl-lactic acid (number average molecular weight: 2,000) were dissolved in 0.6 ml of methylene chloride. After the resulting solution was emulsified and dispersed in 200 ml of a 0.5% aqueous solution of polyvinyl alcohol by a small homogenizer, the resulting dispersion was stirred for about 3 hours to conduct O/W solvent evaporation so that an oil phase was solidified. Microspheres thus formed were collected by a centrifugal separator, washed with purified water, re-dispersed in water and then lyophilized into powder.

EXAMPLE 7

Ten milligrams of dinorphine analog, 2.5 mg of sodium laurate and 100 mg of poly-dl-lactic acid (number average molecular weight: 2,000) were dissolved in 0.3 ml of methylene chloride. The resulting solution was emulsified and dispersed in 100 ml of a 1% aqueous solution of polyvinyl alcohol. Following the procedures of Example 6, solvent evaporation, washing and lyophilization were conducted to obtain powder.

EXAMPLE 8

Ten milligrams of thytropin releasing hormone, 5 mg of sodium palmitate and 100 mg of poly-l-lactic acid (number average molecular weight: 2,000) were dissolved in 0.3 ml of methylene chloride. Following the procedures of Example 6, the resulting solution was subjected to O/W solvent evaporation in 100 ml of a 0.5% aqueous solution of polyvinyl alcohol and lyophilization was then conducted to obtain powder.

EXAMPLE 9

Ten milligrams of neurotensin analog, 9.2 mg of sodium caprylate and 200 mg of poly-dl-lactic acid (number average molecular weight: 2,000) were dissolved in 0.6 ml of a mixed solvent of methylene chloride and ethanol (mixing ratio: 5:1 by volume). Following the procedures of Example 6, the resulting solution was subjected to O/W solvent evaporation in 200 ml of a 0.5% aqueous solution of polyvinyl alcohol and lyophilization was then conducted to obtain powder.

EXAMPLE 10

Ten milligrams of neurotensin analog, 4.6 mg of sodium caprylate and 100 mg of poly-dl-lactic acid (number average molecular weight: 4,000) were dissolved in 0.4 ml of a mixed solvent of methylene chloride and dimethyl sulfoxide (mixing ratio: 5:2 by volume). Following the procedures of Example 6, the resulting solution was subjected to O/W solvent evaporation in 100 ml of a 0.5% aqueous solution of polyvinyl alcohol and lyophilization was then conducted to obtain powder.

COMPARATIVE EXAMPLE 3

Microspheres were produced in a similar manner to Example 6 except for the omission of sodium caprylate.

COMPARATIVE EXAMPLE 4

Microspheres were produced in a similar manner to Example 7 except for the omission of sodium laurate.

COMPARATIVE EXAMPLE 5

Microspheres were produced in a similar manner to Example 8 except for the omission of sodium palmitate.

A description will next be made of an experiment to demonstrate advantegeous effects of the second aspect of the invention in detail.

Experiment (1) Procedure:

The drug content in the microspheres obtained in each of Examples 6–10 and Comparative Examples 3–5 was measured by high-performance liquid chromatography. Their incorporation percentages were compared with one another.

(2) Results:

The results are summarized in Table 2.

TABLE 2

| | Sample | | Incorporation percentage |
|---|---|---|---|
| Invention | Example | 6 | 77.2 |
| | | 7 | 38.6 |
| | | 8 | 29.1 |
| | | 9 | 93.3 |
| | | 10 | 95.1 |
| Control | Comp. Ex. | 3 | 10.4 |
| | | 4 | 12.8 |
| | | 5 | 10.6 |

As is apparent from Table 2, the various microsphere samples obtained by the process according to the second aspect of the present invention each demonstrated a higher incorporation percentage of the corresponding water-soluble drug than the microsphere samples (controls) produced without addition of any fatty acid salt.

EXAMPLE 11

Ten milligrams of neurotensin analog, 100 mg of poly-dl-lactic acid (number average molecular weight: 4,000), 4.6 mg of sodium caprylate and 5 mg of glycerin monocaprate were dissolved in 0.3 ml of a mixed solvent of methylene chloride and ethanol (mixing ratio: 5:1 by volume). After the resulting solution was emulsified and dispersed in 100 ml of a 0.5% aqueous solution of polyvinyl alcohol by a small homogenizer, the resulting dispersion was stirred for about 3 hours to conduct O/W solvent evaporation so that an oil phase was solidified. Microspheres thus formed were collected by a centrifugal separator, washed with purified water, re-dispersed in water and then lyophilized into powder.

EXAMPLE 12

Ten milligrams of neurotensin analog, 100 mg of poly-dl-lactic acid (number average molecular weight: 4,000), 4.6 mg of sodium caprylate and 5 mg of glycerin monooleate were dissolved in 0.3 ml of a mixed solvent of methylene chloride and ethanol (mixing ratio: 5:1 by volume). After the resulting solution was emulsified and dispersed in 100 ml of a 0.5% aqueous solution of polyvinyl alcohol by a small homogenizer, the resulting dispersion was stirred for about 3 hours to conduct O/W solvent evaporation so that an oil phase was solidified. Microspheres thus formed were collected by a centrifugal separator, washed with purified water, re-dispersed in water and then lyophilized into powder.

COMPARATIVE EXAMPLE 6

Ten milligrams of neurotensin analog, 100 mg of poly-dl-lactic acid (number average molecular weight: 4,000) and 4.6 mg of sodium caprylate were dissolved in 0.3 ml of a mixed solvent of methylene chloride and ethanol (mixing ratio: 5:1 by volume). After the resulting solution was emulsified and dispersed in 100 ml of a 0.5% aqueous solution of polyvinyl alcohol by a small homogenizer, the resulting dispersion was stirred for about 3 hours to conduct O/W solvent evaporation so that an oil phase was solidified. Microspheres thus formed were collected by a centrifugal separator, washed with purified water, re-dispersed in water and then lyophilized into powder.

Table 3 illustrates the behavior of release of the drug from each of the microsphere samples which had been obtained by the process according to the third aspect of the present invention in Examples 11 and 12, respectively, and contained the corresponding glycerin fatty acid esters and/or propylene glycol fatty acid ester. Each microsphere was gently stirred in a phosphate buffer of pH 7.4 and the amount of the corresponding drug still remaining in the microspheres was measured by high-performance chromatography.

TABLE 3

| | Percentages of Drugs Remaining in Microspheres | | | | | |
|---|---|---|---|---|---|---|
| Sample Days | 1 | 7 | 14 | 21 | 28 | 42 |
| Comp. Ex. 6 | 95.8 | 91.8 | 90.8 | 84.8 | 66.8 | 47.8 |
| Example 11 | 90.5 | 81.6 | 72.8 | 66.5 | 56.2 | 40.3 |
| 12 | 88.7 | 75.2 | 67.5 | 55.6 | 44.1 | 26.7 |

It is clearly appreciated from Table 3 that microspheres produced by the process according to the third aspect of the present invention release their drug at a constant rate from the initial stage after administration and the release rate varies depending on the substances added.

EXAMPLE 13

Ten milligrams of neurotensin analog, 100 mg of poly-dl-lactic acid (number average molecular weight: 4,000), 4.6 mg of sodium caprylate and 5 mg of propylene glycol monocaprylate were dissolved in 0.3 ml of a mixed solvent of methylene chloride and ethanol (mixing ratio: 5:1 by volume). After the resulting solution was emulsified and dispersed in 100 ml of a 0.5% aqueous solution of polyvinyl alcohol by a small homogenizer, the resulting dispersion was stirred for about 3 hours to conduct O/W solvent evaporation so that an oil phase was solidified. Microspheres thus formed were collected by centrifugation, washed with purified water, re-dispersed in water and then lyophilized into powder.

EXAMPLE 14

Ten milligrams of neurotensin analog, 100 mg of poly-dl-lactic acid (number average molecular weight: 4,000), 4.6 mg of sodium caprylate, 2.5 mg of glycerin monocaprate and 2.5 mg of propylene glycol dicaprylate were dissolved in 0.3 ml of a mixed solvent of methylene chloride and ethanol (mixing ratio: 5:1 by volume). After the resulting solution was emulsified and dispersed in 100 ml of a 0.5% aqueous solution of polyvinyl alcohol by a small homogenizer, the resulting dispersion was stirred for about 3 hours to conduct O/W solvent evaporation so that an oil phase was solidified. Microspheres thus formed were collected by centrifugation, washed with purified water, re-dispersed in water and then lyophilized into powder.

We claim:

1. In a process for the production of drug-containing microspheres using oil-in-water solvent evaporation, wherein the drug is a physiologically active peptide or an antitumor agent, the improvement wherein the oil phase consists essentially of:

(a) a mixed solvent containing a mixture of at least one water-insoluble solvent selected from the group consisting of methylene chloride, chloroform, carbon tetrachloride, dicholorethane, ethyl acetate and cyclohexane and at least one water-miscible solvent selected from the group consisting of methanol, ethanol, n-propyl alcohol, isopropanol, dimethyl sulfoxide and acetonitrile, in which the proportion of the water-miscible solvent in the oil phase is from 5 to 95%; and (b) a fatty acid or a pharmacologically acceptable salt thereof in a ratio of from 0.2 to 1 part by weight of the fatty acid or salt thereof to 1 part by weight of the drug, said fatty acid being selected from the group consisting of butyric acid, valeric acid, caproic acid, enanthic acid, caprylic acid, pelargonic acid, caprylic acid, undecylic acid, lauric acid, tridecylic acid, myristic acid, pentadecylic acid, palmitic acid, heptadecylic acid, stearic acid, nonadecanoic acid, arachic acid, isocrotonic acid, undecylenic acid, oleic acid, elaidic acid, sorbic acid, linoleic acid, linolenic acid and arachidonic acid.

2. The process of claim 1, wherein the fatty acid salt contains at least 4 carbon atoms.

3. The process of claim 1, wherein the fatty acid salt is pharmacologically acceptable and is dissociable in an aqueous solution.

4. The process of claim 3, wherein the fatty acid salt is a sodium or potassium salt.

5. The process of claim 1, wherein the fatty acid salt is selected from the group consisting of sodium butyrate, sodium valerate, sodium caproate, sodium enanthoate, sodium caprylate, sodium pelargonate, sodium caprate, sodium undecylate, sodium laurate, sodium tridecylate, sodium myristate, sodium pentadecylate, sodium palmitate, sodium heptadecylate, sodium stearate, sodium nonadecanoate, sodium arachiate, sodium isocrotonate, sodium undecylenate, sodium oleate, sodium elaidiate, sodium sorbiate, sodium linoleate, sodium linolenate, sodium arachidonate and potassium oleate.

6. In a process for the production of drug-containing microspheres using oil-in-water solvent evaporation, wherein the drug is a physiologically active peptide or an antitumor agent, the improvement wherein the oil phase consists essentially of:

(a) a mixed solvent containing a mixture of at least one water-insoluble solvent selected from the group consisting of methylene chloride, chloroform, carbon tetrachloride, dichloroethane, ethyl acetate and cyclohexane and at least one water-miscible solvent selected from the group consisting of methanol, ethanol, n-propyl alcohol, isopropanol, dimethyl sulfoxide and acetonitrile, in which the proportion of the water-miscible solvent in the oil phase is from 5 to 95%; and (b)(1) at least one glycerin fatty acid ester selected from the group consisting of glycerin monocaprylate, glycerin monocaprate, glycerin monolaurate, glycerin monomyristate, glycerin monopalmitate, glycerin monostearate and glycerin monooleate, or (2) at least one propylene glycol fatty acid ester selected from a group consisting of propylene glycol monocaprylate, propylene glycol monocaprate, propylene glycol monolaurate, propylene glycol monomyristate, propylene glycol monopalmitate, propylene glycol monostearate and propylene glycol monooleate, or (3) mixtures of (1) and (2) above.

7. In a process for the production of drug-containing microspheres using oil-in-water solvent evaporation, wherein the drug is a physiologically active peptide or an antitumor agent, the improvement wherein the oil phase consists essentially of:

(a) a mixed non-aqueous solvent containing a mixture of at least one water-insoluble solvent selected from the group consisting of methylene chloride, chloroform, carbon tetrachloride, dichloroethane, ethyl acetate and cyclohexane and at least one water-miscible solvent selected from the group consisting of methanol, ethanol, n-propyl alcohol, isopropanol, dimethyl sulfoxide and acetonitrile, in which the proportion of the water-miscible solvent in the oil phase is from 5 to 95%;

(b) a fatty acid or a pharmacologically acceptable salt thereof, said fatty acid being selected from the group consisting of butyric acid, valeric acid, caproic acid, enanthic acid, caprylic acid, pelargonic acid, caprylic acid, undecylic acid, lauric acid, tridecylic acid, myristic acid, pentadecylic acid, palmitic acid, heptadecylic acid, stearic acid, nonadecanoic acid, arachic acid, isocrotonic acid, undecylenic acid, oleic acid, elaidic acid, sorbic acid, linoleic acid, linolenic acid and arachidonic acid; and (c)(1) at least one glycerin fatty acid ester selected from the group consisting of glycerin monocaprylate, glycerin monocaprate, glycerin monolaurate, glycerin monomyristate, glycerin monopalmitate, glycerin monostearate and glycerin monooleate, or (2) at least one propylene glycol fatty acid ester selected from a group consisting of propylene glycol monocaprylate, propylene glycol monocaprate, propylene glycol monolaurate, propylene glycol monomyristate, propylene glycol monopalmitate, propylene glycol monostearate and propylene glycol monooleate, or (3) mixtures of (1) and (2) above.

8. A process for the production of drug-containing microspheres, wherein the drug is a physiologically active peptide or an antitumor agent, which consists essentially of adding to the drug a substantially water insoluble high molecular polymer having in vivo degradability or biocompatibility and which has film-forming properties, capable of encapsulating said drug, said substantially water insoluble high molecular polymer being at least one member selected from the group consisting of polylactic acid, polyglycolic acid, polystyrene and polyacrylic acid in the form of physical mixtures or copolymers thereof, dissolving or dispersing the resulting mixture in a mixed solvent of at least one water-insoluble solvent selected from the group consisting of methylene chloride, chloroform, carbon tetrachloride, dicholorethane, ethyl acetate and cyclohexane and at least one water-miscible solvent selected from the group consisting of methanol, ethanol, n-propyl alcohol, isopropanol, dimethyl sulfoxide and acetonitrile to form an oil phase, in which the proportion of the water-miscible solvent in the oil phase is from 5 to 95%, emulsifying and dispersing the oil phase in an aqueous solution of polyvinyl alcohol, and subjecting the resulting dispersion to oil-in-water solvent evaporation.

9. The process of claim 8, wherein the high molecular polymer having in vivo degradability is selected from the group consisting of polylactic acids, polyglycolic acids, poly-α-cyanoacrylic acid esters, poly-β-hydroxybutyric acids, polyorthoesters, thermally denatured collagen, formaldehyde-crosslinked collagen, gelatin, albumin, and enzyme-modified fibrin.

10. The process of claim 8, wherein the high molecular polymer having bio-compatibility is selected from the group consisting of polystyrene, polyacrylic acid, polymethacrylic acid, ethylcellulose, polyacrylamide, maleic anhydride copolymers and polyurethanes.

11. A process for the production of drug-containing microspheres, which consisting essentially of:

(i) adding to a drug a substantially water insoluble high molecular polymer having in vivo degradability or bio-compatibility and which has film forming properties, capable of encapsulating said drug, said substantially water insoluble high molecular polymer being at least one member selected from the group consisting of polylactic acid, polyglycolic acid, polystyrene and polyacrylic acid in the form of physical mixtures or copolymers thereof;

(ii) adding (a) a mixed solvent of at least one water-insoluble solvent selected from the group consisting of methylene chloride, chloroform, carbon tetrachloride, dicholorethane, ethyl acetate and cyclohexane and at least one water-miscible solvent selected from the group consisting of methanol, ethanol, n-propyl alcohol, isopropanol, dimethyl sulfoxide and acetonitrile and (b) a fatty acid or a pharmacologically acceptable salt thereof to the resulting mixture to form an oil phase, in which the proportion of the water-miscible solvent in the oil phase is from 5 to 95%, and in a ratio of from 0.2 to 1 part by weight of the fatty acid or salt thereof to 1 part by weight of the drug, said fatty acid being selected from the group consisting of butyric acid, valeric acid, caproic acid, enanthic acid, caprylic acid, pelargonic acid, caprylic acid, undecylic acid, lauric acid, tridecylic acid, myristic acid, pentadecylic acid, palmitic acid, heptadecylic acid, stearic acid, nonadecanoic acid, arachic acid, isocrotonic acid, undecylenic acid, oleic acid, elaidic acid, sorbic acid, linoleic acid, linolenic acid and arachidonic acid;

(iii) emulsifying and dispersing the oil phase in an emulsifier-containing, aqueous solution; and (iv) subjecting the resulting dispersion to oil-in-water solvent evaporation.

12. The process of claim 7 wherein the fatty acid or pharmacologically acceptable salt thereof is present in a ratio of from 0.2 to 2 part by weight to 1 part by weight of the drug.

13. The process of claim 8 wherein the substantially water insoluble high molecular polymer is a lactic acid-glycolic acid copolymer.

14. The process of claim 11 wherein the substantially water insoluble high molecular polymer is a lactic acid-glycolic acid copolymer.

* * * * *